United States Patent
Bredno et al.

(10) Patent No.: US 9,576,376 B2
(45) Date of Patent: Feb. 21, 2017

(54) INTERACTIVE METHOD OF LOCATING A MIRROR LINE FOR USE IN DETERMINING ASYMMETRY OF AN IMAGE

(75) Inventors: Joerg Bredno, San Francisco, CA (US); Mark Olszewski, Solon, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1492 days.

(21) Appl. No.: 13/054,503

(22) PCT Filed: Jul. 14, 2009

(86) PCT No.: PCT/IB2009/053057
§ 371 (c)(1),
(2), (4) Date: Jan. 17, 2011

(87) PCT Pub. No.: WO2010/015956
PCT Pub. Date: Feb. 11, 2010

(65) Prior Publication Data
US 2011/0116702 A1 May 19, 2011

Related U.S. Application Data

(60) Provisional application No. 61/086,827, filed on Aug. 7, 2008.

(51) Int. Cl.
*G06K 9/00* (2006.01)
*G06T 7/60* (2006.01)
*G06F 19/00* (2011.01)

(52) U.S. Cl.
CPC .......... *G06T 7/608* (2013.01); *G06F 19/3406* (2013.01); *G06T 2207/10072* (2013.01); *G06T 2207/30016* (2013.01)

(58) Field of Classification Search
CPC .......... G06F 19/3406; G06T 2207/10072; G06T 2207/30016; G06T 7/608
USPC .................... 382/128–132; 600/424
See application file for complete search history.

(56) References Cited

U.S. PATENT DOCUMENTS

| | | | |
|---|---|---|---|
| 2005/0283070 A1 | 12/2005 | Imielinska et al. | |
| 2008/0021502 A1* | 1/2008 | Imielinska | A61B 6/032 607/1 |
| 2008/0095419 A1* | 4/2008 | Volkau | G01R 33/56 382/131 |

FOREIGN PATENT DOCUMENTS

| | | |
|---|---|---|
| WO | 03060827 A1 | 7/2003 |
| WO | 2007095284 A2 | 8/2007 |

OTHER PUBLICATIONS

Stephen et al ("Accurate Robust Symmetry Estimation", MICCAI 99, LNCS 1679, pp. 308-317, 1999).*

(Continued)

*Primary Examiner* — Amara Abdi

(57) ABSTRACT

A method and apparatus are provided for locating a mirror line for conducting a mirror analysis of an image by reflecting extracted image content from a portion of the image on one side of the mirror line and overlaying this reflected image content onto the corresponding portion of the image on the opposing side of the mirror line. The extracted image content that is reflected onto the corresponding portion of the image on the opposite side of the mirror line is continuously updated in real-time as the user manipulates the location or orientation of the mirror line.

29 Claims, 4 Drawing Sheets

(56) References Cited

OTHER PUBLICATIONS

Thirion, J-P., et al.; Statistical Analysis of Dissymmetry in Volumetric Medical Images; 1997; INRIA; No. 3178. http://www.inria.fr/Equipes/EPIDAURE-eng.html.
Martel et al: "Perfusion MRI of Infarcted and Noninfarcted Brain Tissue in Stroke: A Comparison of Conventional Hemodynamic Imaging and Factor Analysis of Dynamic Studies"; Investigative Radiology, 2001, vol. 36, No. 7, pp. 378-385.
Grigaitis et al: "Determination of Symmetry Axis"; October 2004, Dept. of Radio Electronics, Vilnius Gediminas Technical University, Lithuania, Retrieved From the Internet:http://www.grigaitis.eu/?page_id=111, 4 Page Document.
Smith et al: "Accurate Robust Symmetry Estimation"; 1999 MICCAI '99, LNCS 1679, pp. 308-317.

\* cited by examiner

INTERACTIVE METHOD OF LOCATING A MIRROR LINE FOR USE IN DETERMINING ASYMMETRY OF AN IMAGE

The present application relates generally to the imaging arts and more particularly to an interactive method of determining a mirror line for use in determining asymmetry of an image. The application subject matter finds particular use with functional imaging (i.e., anatomical imaging data that has been combined with additional physiological data), such as brain perfusion imaging, and will be described with particular reference thereto. However, it could also be used in connection with anatomical imaging alone or physiological imaging alone. The application subject matter could be used with images obtained via various imaging modalities, such as computed tomography (CT) imaging systems, magnetic resonance (MR) imaging systems, positron emission tomography (PET) imaging systems, single photon emission computed tomography (SPECT) imaging systems, or other imaging modalities and combinations of imaging modalities.

Various anatomical structures and physiological functions, such as blood flow in the human brain, exhibit approximate symmetry on each side of a mirror line. Due to this approximate symmetry, certain physiological or pathological abnormalities can be detected by identifying any asymmetries in a medical image of such anatomical structures or physiological functions. Such asymmetries can result from a portion on one side of the mirror line being healthy and a corresponding portion on the other side being unhealthy. These determinations are advantageously not affected by inter-patient variations, such as hemodynamic variations from patient to patient.

To conduct a mirror comparison of an image, such as hemispheric comparison of a brain slice image, a mirror line that divides the image into approximately equal halves must first be extracted. Currently, automated (i.e., software based) and manual methods exist for extracting a mirror line or center line from an image. However, many images, such as brain slice images, frequently do not exhibit exact symmetry, but rather exhibit approximate symmetry with various asymmetrical aspects. Such asymmetrical aspects can result from normal anatomical variability, patient movement, or improper patient placement or orientation during the imaging process.

Accordingly, it would be desirable to provide a method and apparatus that allow for the manipulation and correction of a mirror line to account for these asymmetrical aspects. According to one aspect of the invention an interactive method and apparatus are provided for locating a mirror line for an image by reflecting extracted image content from a portion of the image on one side of the mirror line and overlaying this reflected image content onto the corresponding portion of the image on the opposing side of the mirror line. The extracted image content that is reflected onto the corresponding portion of the image on the opposite side of the mirror line may be continuously updated in real-time as the user manipulates the location or orientation of the mirror line.

The method and apparatus are especially useful in brain perfusion imaging, but may be used in other contexts as well. The method and apparatus for locating a mirror line described herein provide for more accurate placement of the mirror line or center line for use in determining the asymmetry of an image. Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
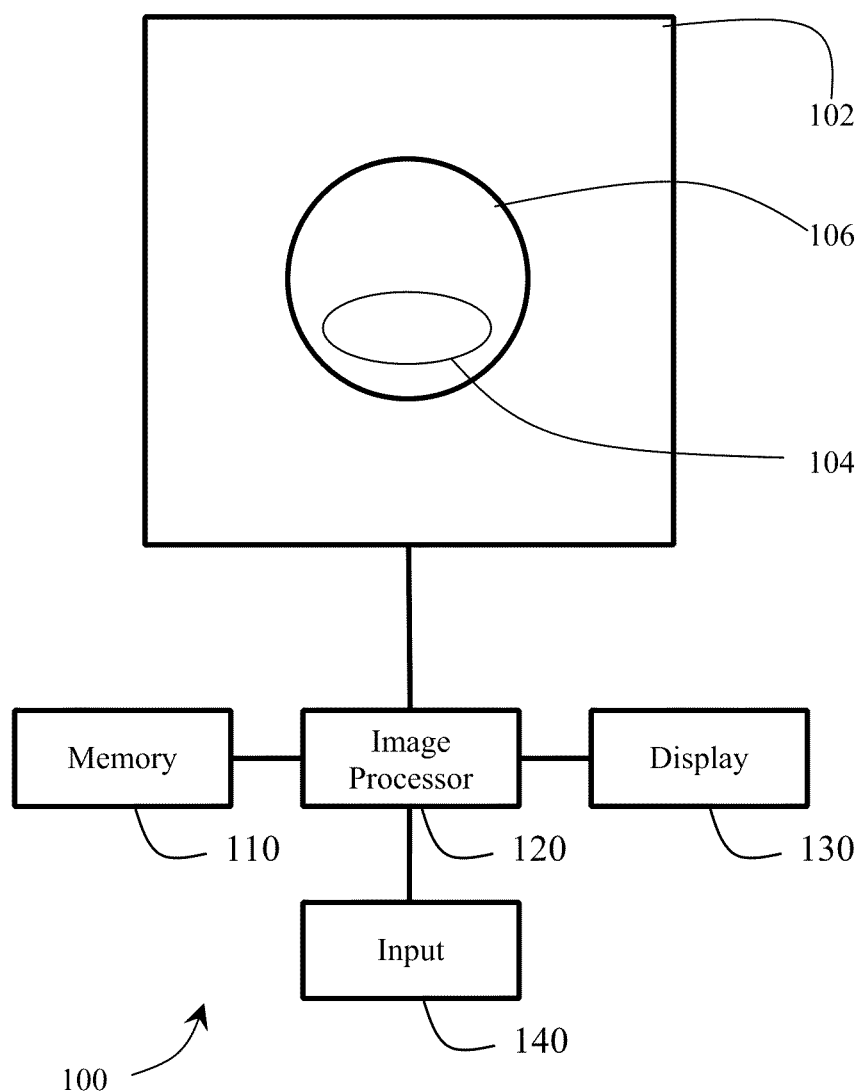
FIG. 1 is an exemplary imaging system.

Currently, various imaging systems are used to obtain certain functional image data (i.e., anatomical imaging data that has been combined with additional physiological data) from an imaged subject, such as image data relating to perfusion parameters. These kinds of imaging systems include CT, MR, PET and SPECT imaging systems. An exemplary imaging system 100 is shown in FIG. 1. As already mentioned, however, the imaging method and apparatus disclosed herein also have application in connection with various other kinds of imaging systems or combinations of imaging systems other than those expressly discussed herein.

As illustrated in FIG. 1 an exemplary imaging system 100 includes an imaging device 102, such as a CT, MR, PET or SPECT imaging device. A representative subject to be imaged is shown at 104 in FIG. 1, partially received in an aperture 106 in the imaging device 102. The image data obtained by the imaging device 102 is stored by an imaging data processor 120 in a memory 110. The image data stored in the memory 110 is processed by the imaging data processor 120. The processor 120 generates an image of the imaged subject 104, according to a mathematical algorithm or algorithms. The image can be displayed on an associated display 130. For example, if the imaging system 100 is a CT imaging system, the processor 120 receives X-ray data from a CT imaging device 102 to generate CT images. A user input 140 may be provided for a user to control the image processor 120.

The aforementioned functions can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as memory 110, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the memory 110. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

As mentioned previously, one prevalent type of functional imaging that is currently conducted is perfusion imaging. One application for which such perfusion imaging has proved useful, is with detecting abnormalities of a patient's brain, particularly in connection with the diagnosis and treatment of strokes. Various therapy decisions made in connection with ischemic strokes often require the accurate and precise identification and assessment of normal brain tissue (not effected by the ischemic event), infarct core (dead brain tissue), ischemic penumbra (dysfunctional tissue that may be salvageable through intervention or reperfusion therapy), and parenchymal vessel wall status (blood-brain-barrier break-down indicating increased risk of hemorrhagic transform). However, due to large inter-patient variability with respect to perfusion parameters, the use of absolute perfusion measurements such as mean transit time (MTT), cerebral blood flow (CBF), and cerebral blood volume (CBV), can lead to the imperfect classification of imaged brain tissue. In other words, a certain perfusion parameter value that corresponds to normal brain tissue in one patient may not be indicative of normal brain tissue in another patient.

Healthy human brains exhibit an approximate bilateral symmetry with respect to the inter-hemispheric fissure that bisects the brain, known as the mid-saggital plane (MSP). Due to this approximate symmetry of healthy brains, certain brain abnormalities can be detected by identifying any brain asymmetries through a hemispheric comparison. The use of such hemispheric comparisons to detect brain abnormalities is advantageous due to the fact that such comparisons are not affected by inter-patient hemodynamic variations. Furthermore, hemispheric comparisons are also advantageous for their ability to account for physiological differences in grey and white brain matter that are not easily distinguished from CT, MR, PET, SPECT images.

Different types of tissue can appear very similar in an anatomical image. It is not easily possible to delineate areas of grey and white matter in an uncontrasted CT image as they appear with very similar greylevels and textures. Even when appearing similar in the anatomical image, these different types of tissue can however have different physiological "normal" values, such as for blood flow. A pathological change can even be the loss of differences in appearance and blood flow of white and gray matter. Especially in this case, no valid assumption of a "normal" flow value is available—it is not even known what tissue type is present in some regions of the image. The unaffected hemisphere, however, gives a good indication of what should be happening in the affected hemisphere.

To conduct a hemispheric comparison of a brain slice image, a mirror line that divides the brain into approximately equal hemispheres must first be extracted. Currently, automated (i.e., software based) and manual methods exist for extracting a mirror line or center line from a brain slice image. However, as mentioned previously, frequently brain slice images do not exhibit exact symmetry, but rather exhibit approximate symmetry with various asymmetrical aspects. This can be exacerbated after a stroke, which often leads to brain swelling in the hemisphere where the stroke occurred.

Figure 2:
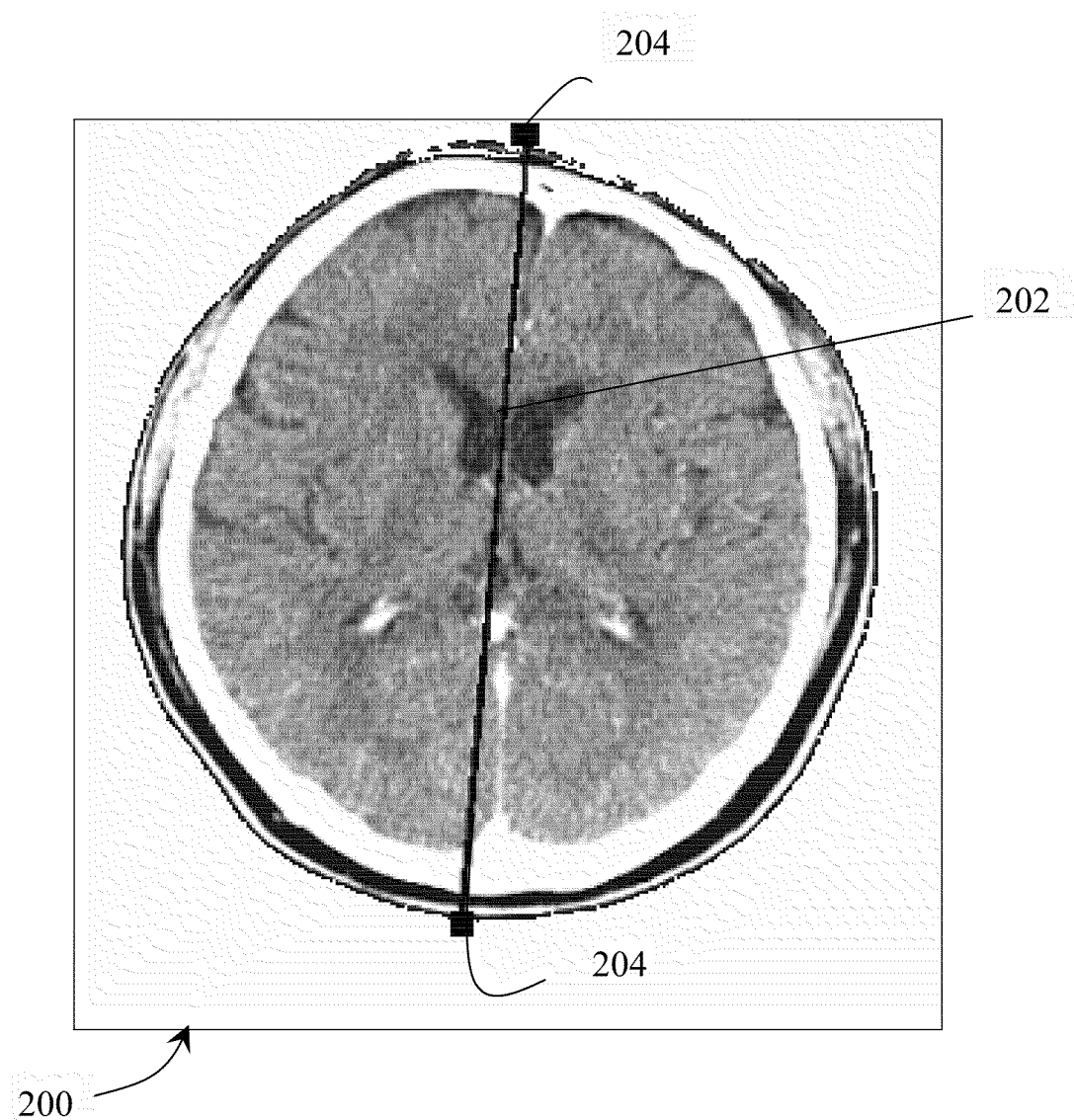
FIG. 2 is an exemplary screen shot from a currently available software program for locating mirror lines for brain slice images.

Some current methods provide for the manipulation of the mirror line or center line to account for these asymmetrical aspects. An exemplary screen shot 200 from one such currently available software program is illustrated in FIG. 2. This software program allows for a user to manipulate the location and orientation of the mirror line 202 with a computer mouse or other computer input interface (e.g., by using a computer mouse to drag the endpoints 204 of the mirror line 202 to the desired location) to account for asymmetrical aspects of the brain slice image. However, this manipulation of the mirror line 202 is based solely upon the user's visual impression of the two hemispheres of the brain slice image and where the mirror line should be placed to effectively divide the brain slice image along an axis of symmetry. The effectiveness of this method is limited by the inherent limitations and subjective nature of the user's visual impression of the image and the user's ability to properly locate the mirror line in response to their visual impression.

Figure 3:
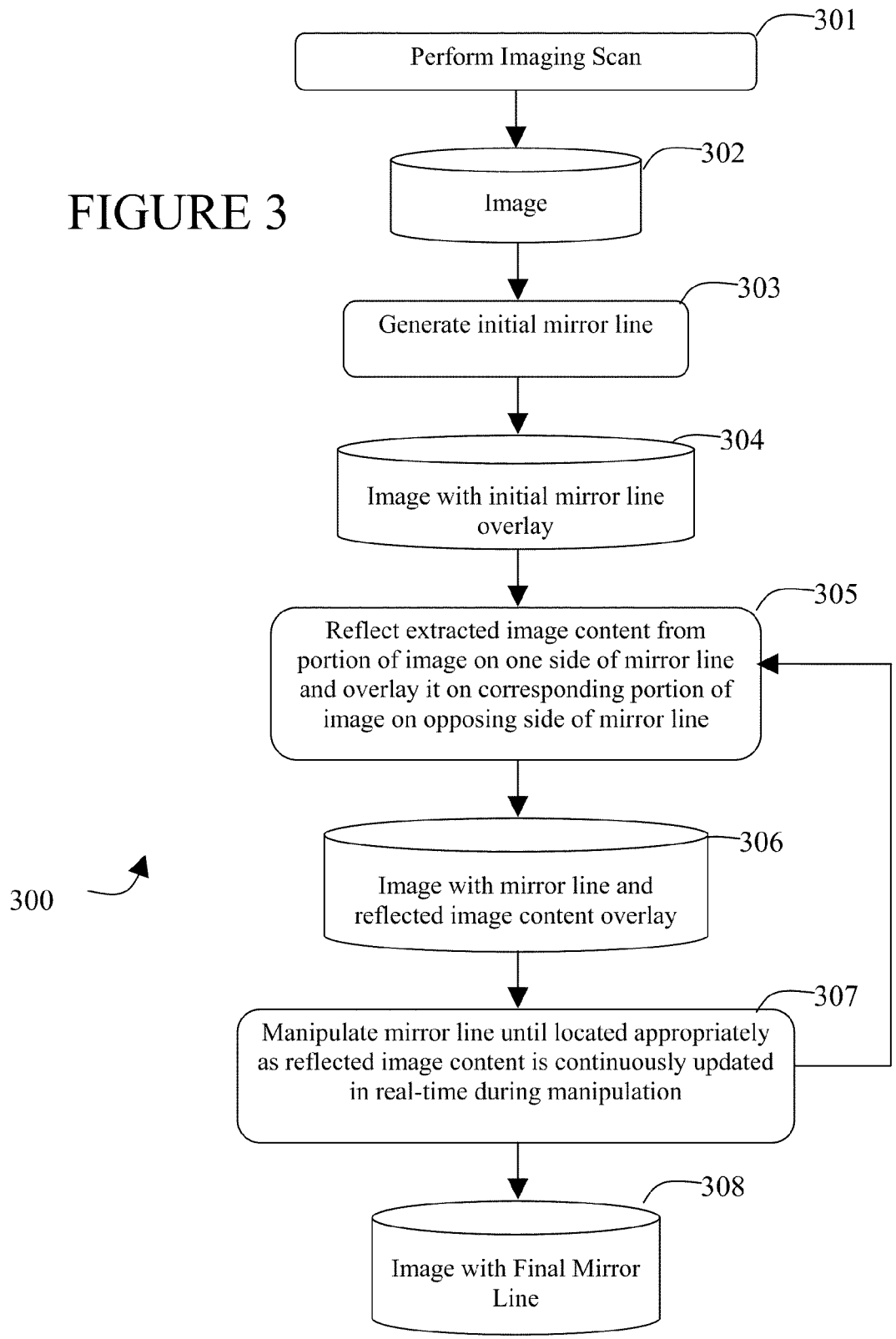
FIG. 3 illustrates an exemplary process of locating a mirror line for use in determining asymmetry of an image.

In accordance with the present invention, a mirror line for use in determining asymmetry of an image, such as a brain slice image, may be generated and manipulated in a process 300 as shown in FIG. 3. The imaging device 102 is used to perform 301 an imaging scan and generate an image 302. In one exemplary embodiment, the image 302 is a brain perfusion image. As mentioned previously, the process 300 disclosed herein may be used with a variety of imaging systems, such as CT, MR, PET or SPECT imaging systems, and combinations thereof. For example, a functional image may be produced by combining an anatomical image obtained from a CT imaging system with additional physiological data obtained via another imaging system, such as an MR imaging system. Once the desired image 302 is obtained, an initial mirror line is generated 303 from the image 302 using currently available software to generate an image with an initial mirror line overlay 304. The mirror line divides the image into at least a first image portion and a second image portion.

Figure 4:
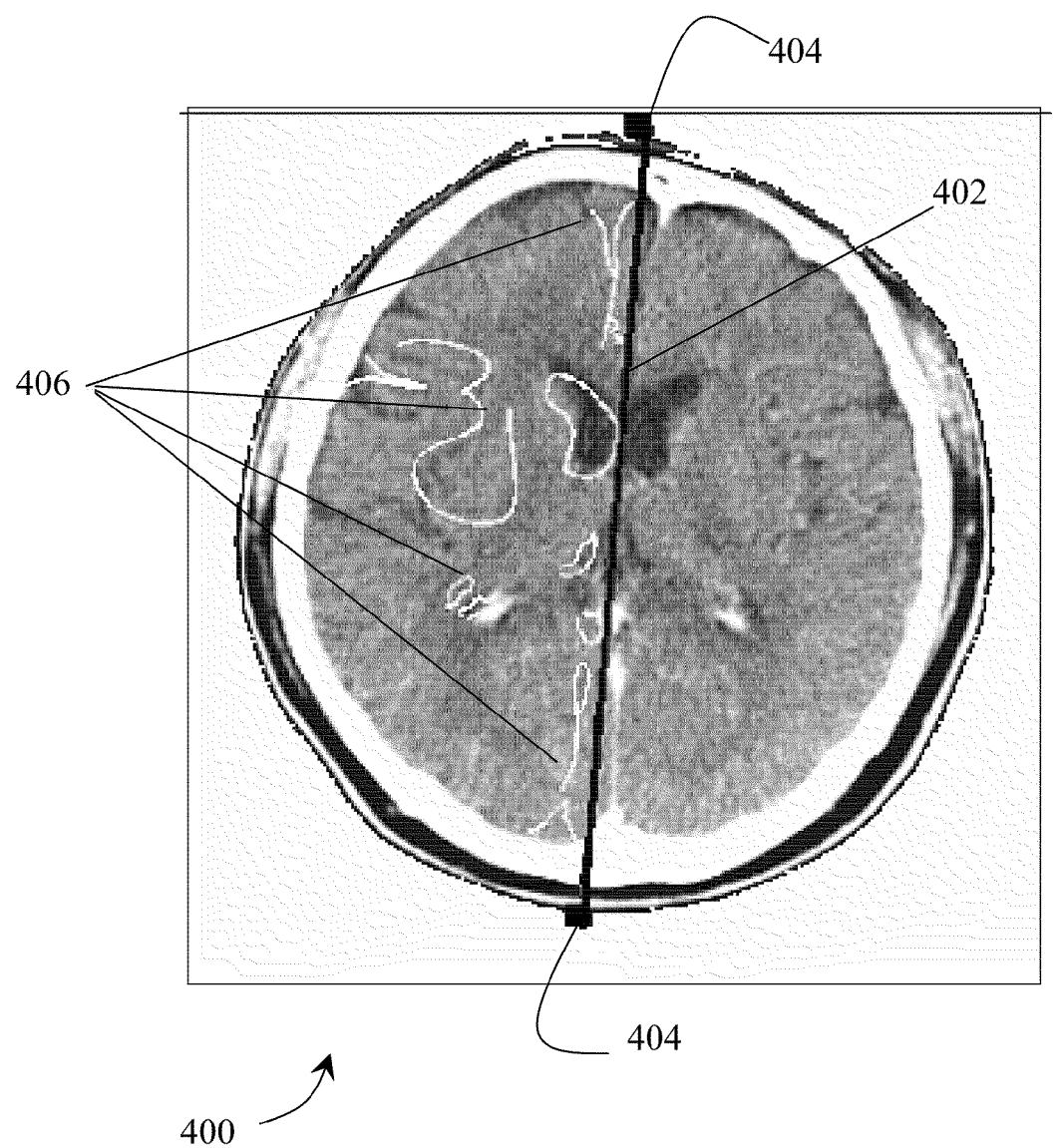
FIG. 4 is an exemplary screen shot from a software program in accordance with one embodiment of the present invention.

Referring now to FIG. 4, an exemplary screen shot 400 from a software program in accordance with one embodiment of the present invention is illustrated. The screen shot 400 includes a brain slice image with a mirror line 402 overlaying the image. The software program allows for a user to manipulate the location and orientation of the mirror line 402 with a computer mouse or other computer input interface (e.g., by using a computer mouse to drag the endpoints 404 of the mirror line 402 to the desired location). Although the mirror line 402 is shown as a straight line that intersects the entire image, it should be understood that additional embodiments may include a mirror line that is made up of a shorter line segment that does not intersect the entire image, a plurality of line segments, or a curve or other shape. Also, it should be apparent that the mirror line may divide the image vertically or horizontally or in any angular orientation with respect to the image (e.g., at a 45° angle). Finally, additional embodiments may include more than one mirror line. For example, one mirror line may divide the image vertically and an additional mirror line may divide the image horizontally.

Referring again to FIG. 3, once the image with initial mirror line overlay 304 is generated, image content is extracted from one of the first or second image portions. The image content may be extracted from either of the first or second image portions, or both, depending upon the user's preference. This extracted image content is then reflected 305 onto the corresponding image portion on the opposing side of the mirror line 402 to generate an image with an overlay of the mirror line and reflected image content 306. This reflection of the extracted image content may be performed using a variety of known methods currently employed in connection with interactive image registration. For example, as illustrated in FIG. 4, the extracted image content 406 may be edge contours extracted from one hemisphere of a brain slice image (on the right in FIG. 4) that are then reflected and overlaid over the opposite hemisphere (on the left in FIG. 4). In addition, a subtraction result or a checkerboard display of both original and mirrored image data may be employed in additional embodiments. It should be apparent to those skilled in the art that additional methods for reflecting extracted image content from one portion of the image onto the opposing portion of the image could also be used.

As the user manipulates the mirror line 402, the extracted image content 406 being reflected onto the corresponding portion of the image on the opposing side of the mirror line 402 is continuously updated and overlaid over the image. In additional embodiments, the reflected extracted image content may not be continuously updated, but rather it may be updated periodically. In this manner, a user will receive real time interactive visual feedback as the location or orientation of the mirror line 402 is manipulated. Accordingly, the mirror line 402 is manipulated 307 in this way until the user is satisfied with the location or orientation of the mirror line based on the alignment of the reflected image content overlay with the underlying image (i.e., in an iterative process). For example, referring again to the screen shot 400 of FIG. 4, the user can manipulate the location or orientation of the mirror line 402 until the user is satisfied that the edge contours 406 extracted from the right hemisphere properly aligns with the corresponding edge contours of the left hemisphere that they are overlaid over. Due to this interactive visual feedback based upon extracted image content, the mirror line 402 may be more accurately placed than if it were located simply based upon a user's subjective visual impression.

In various embodiments of the proposed process, the user can pre-select areas of the image where a mirror analysis of the image would be most relevant. For example, the user may select a certain area of the hemispheres of a brain slice image where the user feels a hemispheric comparison would be most relevant. Extracted image content, such as the edge contours 406 previously described, from only these pre-selected areas could then be reflected and overlaid on the corresponding portion of the opposing hemisphere. In this manner, the user could ensure that mirror line 402 is as accurate as possible with respect to the pre-selected area of interest and high-quality relative values are provided for the pre-selected area.

Once the user is satisfied with the location of the mirror line, an image with final mirror line 308 is generated. The final mirror line is then utilized in conducting an analysis of the image for any asymmetry. Preferably, the overlaying of extracted image content feature is active only during interactive editing of the mirror line.

The process described above includes the extraction and reflecting of image data from one side of the image onto the other side for use with the location of the mirror line. However, additional embodiments of the process may include multiple steps of extracting and reflecting image data. For example, image content from an area of the first image portion may be reflected onto the second image portion to locate the mirror line in a first position. Then extracted image content from the second image portion may be reflected onto the first image portion to further refine the location of the mirror line. In yet further additional embodiments, image content could be extracted from both the first image portion and second image portion and simultaneously mirrored and overlaid onto the opposing side for use with the location of the mirror line.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various components and arrangements of components, and in various steps and arrangements of steps. The drawings are only for purposes of illustrating the preferred embodiments and are not to be construed as limiting the invention.

The invention claimed is:

1. A method of locating a mirror line for conducting a symmetry analysis of an image, the method comprising:
    utilizing the image to generate a mirror line in a first location, the mirror line dividing the image into at least a first image portion and a second image portion;
    extracting image content from at least one of the first or second image portions;
    reflecting the extracted image content onto the other of the first or second image portions based upon the first location of the mirror line;
    manipulating the location of the mirror line with respect to the image to move the mirror line to a second location;
    updating the reflected extracted image content based upon the second location of the mirror line; and
    generating a final mirror line based upon an analysis of the reflected extracted image content with the mirror line in the second location.

2. The method of claim 1, wherein the step of reflecting the extracted image content includes the reflecting of extracted edge contours.

3. The method of claim 1, wherein the step of reflecting the extracted image content includes the use of a subtraction method.

4. The method of claim 1, wherein the step of reflecting the extracted image content includes the use of a checkerboard display method.

5. The method of claim 1, wherein the reflected extracted image content is updated continuously in real time as the location of the mirror line is manipulated based upon the then current location of the mirror line.

6. The method of claim 1, further comprising the step of utilizing the final mirror line to conduct a symmetry analysis of the image.

7. The method of claim 1, wherein the step of extracting image content includes extracting image content from both the first image portion and the second image portion; and wherein the step of reflecting the extracted image content includes reflecting the image content extracted from the first image portion onto the second image portion and reflecting the image content extracted from the second image portion onto the first image portion.

8. The method of claim 1, wherein the mirror line comprises a curve or a plurality of line segments.

9. The method of claim 1, wherein a portion of at least one of the first or second image portions is selected by a user, wherein image content is extracted from the selected portion, and wherein the extracted image content from the selected portion is reflected onto a corresponding portion of the other of the first or second image portions based upon the location of the mirror line.

10. The method of claim 1, wherein the image includes CT, MR, PET or SPECT image data.

11. An imaging system comprising an apparatus for locating a mirror line for conducting a symmetry analysis of an image, the apparatus comprising a computer readable medium comprising logic to:
utilize an image from the imaging system to generate a mirror line, the mirror line dividing the image into at least a first image portion and a second image portion,
extract image content from at least one of the first or second image portions,
reflect the extracted image content onto the other of the first or second image portions based upon the location of the mirror line,
manipulate the location of the mirror line with respect to the image, and
update the reflected image content based upon the then current location of the manipulated mirror line until a final mirror line is generated.

12. The imaging system of claim 11, wherein the reflecting of the extracted image content includes the reflecting of extracted edge contours.

13. The imaging system of claim 11, wherein the reflecting of the extracted image content includes the use of a subtraction method.

14. The imaging system of claim 11, wherein the reflecting of the extracted image content includes the use of a checkerboard display method.

15. The imaging system of claim 11, wherein the computer readable medium comprises logic to continuously update the reflected extracted image content in real time as the location of the mirror line is manipulated based upon the then current location of the mirror line.

16. The imaging system of claim 11, wherein the computer readable medium comprises logic to utilize the final mirror line to conduct a symmetry analysis of the image.

17. The imaging system of claim 11, wherein the computer readable medium comprises logic to extract image content from both the first image portion and the second image portion, reflect the extracted image content from the first image portion onto the second image portion, and reflect the extracted image content from the second image portion onto the first image portion.

18. The imaging system of claim 11, wherein the mirror line comprises a curve or a plurality of line segments.

19. The imaging system of claim 11, wherein a portion of at least one of the first or second image portions is selected by a user, wherein image content is extracted from the selected portion, and wherein the extracted image content from the selected portion is reflected onto a corresponding portion of the other of the first or second image portions based upon the location of the mirror line.

20. The imaging system of claim 11, wherein the imaging system includes a CT, MR, PET or SPECT imaging device.

21. An apparatus for locating a mirror line for conducting a symmetry analysis of an image, the apparatus comprising a computer readable medium comprising logic to:
utilize the image to generate a mirror line, the mirror line dividing the image into at least a first image portion and a second image portion,
extract image content from at least one of the first or second image portions,
reflect the extracted image content onto the other of the first or second image portions based upon the location of the mirror line,
manipulate the location of the mirror line with respect to the image, and
update the reflected image content based upon the then current location of the manipulated mirror line until a final mirror line is generated.

22. The apparatus of claim 21, wherein the reflecting of the extracted image content includes the reflecting of extracted edge contours.

23. The apparatus of claim 21, wherein the reflecting of the extracted image content includes the use of a subtraction method.

24. The apparatus of claim 21, wherein the reflecting of the extracted image content includes the use of a checkerboard display method.

25. The apparatus of claim 21, wherein the computer readable medium comprises logic to continuously update the reflected extracted image content in real time as the location of the mirror line is manipulated based upon the then current location of the mirror line.

26. The apparatus of claim 21, wherein the computer readable medium comprises logic to utilize the final mirror line to conduct a symmetry analysis of the image.

27. The apparatus of claim 21, wherein the computer readable medium comprises logic to extract image content from both the first image portion and the second image portion, reflect the extracted image content from the first image portion onto the second image portion, and reflect the extracted image content from the second image portion onto the first image portion.

28. The apparatus of claim 21, wherein the mirror line comprises a curve or a plurality of line segments.

29. The apparatus of claim 21, wherein a portion of at least one of the first or second image portions is selected by a user, wherein image content is extracted from the selected portion, and wherein the extracted image content from the selected portion is reflected onto a corresponding portion of the other of the first or second image portions based upon the location of the mirror line.

* * * * *